United States Patent
Perkins et al.

(10) Patent No.: US 10,150,141 B2
(45) Date of Patent: Dec. 11, 2018

(54) MANUFACTURING PROCESS FOR INTEGRATED COMPUTATIONAL ELEMENTS

(71) Applicant: Halliburton Energy Services, Inc., Houston, TX (US)

(72) Inventors: David L. Perkins, The Woodlands, TX (US); Michael T. Pelletier, Houston, TX (US); James M. Price, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 277 days.

(21) Appl. No.: 14/414,456

(22) PCT Filed: Mar. 21, 2014

(86) PCT No.: PCT/US2014/031454
§ 371 (c)(1),
(2) Date: Jan. 13, 2015

(87) PCT Pub. No.: WO2015/142353
PCT Pub. Date: Sep. 24, 2015

(65) Prior Publication Data
US 2016/0282509 A1    Sep. 29, 2016

(51) Int. Cl.
*B05D 7/00* (2006.01)
*C23C 18/16* (2006.01)
(Continued)

(52) U.S. Cl.
CPC ............ *B05D 7/50* (2013.01); *B32B 38/0004* (2013.01); *C23C 16/45525* (2013.01);
(Continued)

(58) Field of Classification Search
CPC .... B05D 7/50; B05D 7/52; B05D 7/56; C23C 18/165
See application file for complete search history.

(56) References Cited

U.S. PATENT DOCUMENTS

| | | | |
|---|---|---|---|
| 5,789,040 A | 8/1998 | Martinu et al. | |
| 6,391,400 B1 * | 5/2002 | Russell | B32B 17/10 296/84.1 |

(Continued)

FOREIGN PATENT DOCUMENTS

| | | |
|---|---|---|
| WO | 2012108885 A1 | 8/2012 |
| WO | 2015142353 A1 | 9/2015 |

OTHER PUBLICATIONS

International Search Report and Written Opinion for PCT/US2014/031454 dated Dec. 19, 2014.

*Primary Examiner* — Christopher T Schatz
(74) *Attorney, Agent, or Firm* — Alan Bryson; Tumey L.L.P.

(57) ABSTRACT

Disclosed are methods of fabricating an integrated computational element for use in an optical computing device. One method includes providing a substrate that has a first surface and a second surface substantially opposite the first surface, depositing multiple optical thin films on the first and second surfaces of the substrate via a thin film deposition process, and thereby generating a multilayer film stack device, cleaving the substrate to produce at least two optical thin film stacks, and securing one or more of the at least two optical thin film stacks to a secondary optical element for use as an integrated computational element (ICE).

14 Claims, 4 Drawing Sheets

(51) Int. Cl.
  *B32B 38/00* (2006.01)
  *G01N 21/27* (2006.01)
  *G01N 21/31* (2006.01)
  *G01N 21/3577* (2014.01)
  *G01N 21/85* (2006.01)
  *G02B 27/00* (2006.01)
  *C23C 16/455* (2006.01)
  *E21B 49/08* (2006.01)
  *G01V 8/10* (2006.01)
  G01N 21/3581 (2014.01)
  G01N 21/359 (2014.01)
  G01N 21/64 (2006.01)
  G01N 21/65 (2006.01)
  G01J 3/12 (2006.01)

(52) U.S. Cl.
  CPC ............ *C23C 18/165* (2013.01); *E21B 49/08* (2013.01); *G01N 21/274* (2013.01); *G01N 21/31* (2013.01); *G01N 21/3577* (2013.01); *G01N 21/85* (2013.01); *G01V 8/10* (2013.01); *G02B 27/0012* (2013.01); *G01J 2003/1213* (2013.01); *G01J 2003/1282* (2013.01); *G01N 21/359* (2013.01); *G01N 21/3581* (2013.01); *G01N 21/645* (2013.01); *G01N 21/65* (2013.01); *G01N 2021/317* (2013.01); *G01N 2021/3129* (2013.01); *G01N 2021/3133* (2013.01); *G01N 2021/3177* (2013.01)

(56) References Cited

U.S. PATENT DOCUMENTS

| | | | |
|---|---|---|---|
| 2006/0187608 A1* | 8/2006 | Stark | C03C 27/08 361/202 |
| 2006/0245056 A1 | 11/2006 | Lin | |
| 2007/0134459 A1 | 6/2007 | Hubert et al. | |
| 2007/0240548 A1* | 10/2007 | Pape | B26D 5/00 83/76.1 |
| 2007/0298594 A1* | 12/2007 | Mizushima | H01L 21/02381 438/479 |
| 2010/0171406 A1* | 7/2010 | Morino | H05K 9/0088 313/110 |
| 2011/0169119 A1* | 7/2011 | Greer | H01L 31/02165 257/432 |
| 2012/0150451 A1 | 6/2012 | Skinner et al. | |
| 2013/0078441 A1 | 3/2013 | Abbott, Jr. et al. | |
| 2013/0284900 A1 | 10/2013 | Freese et al. | |

\* cited by examiner

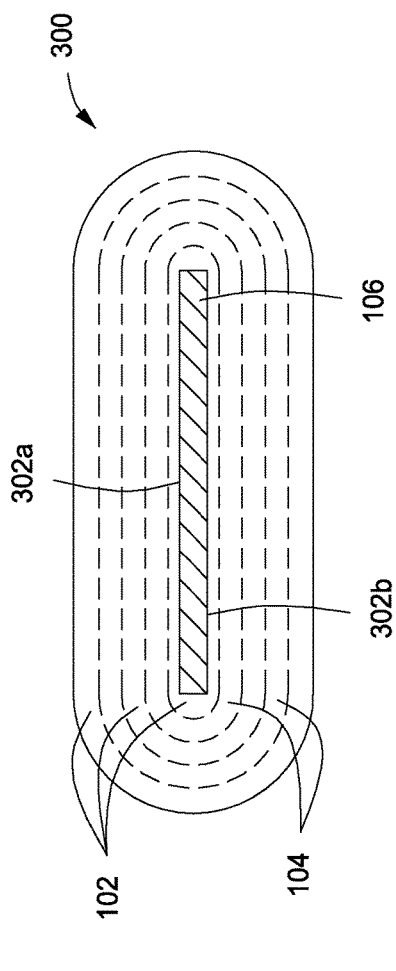
FIG. 3
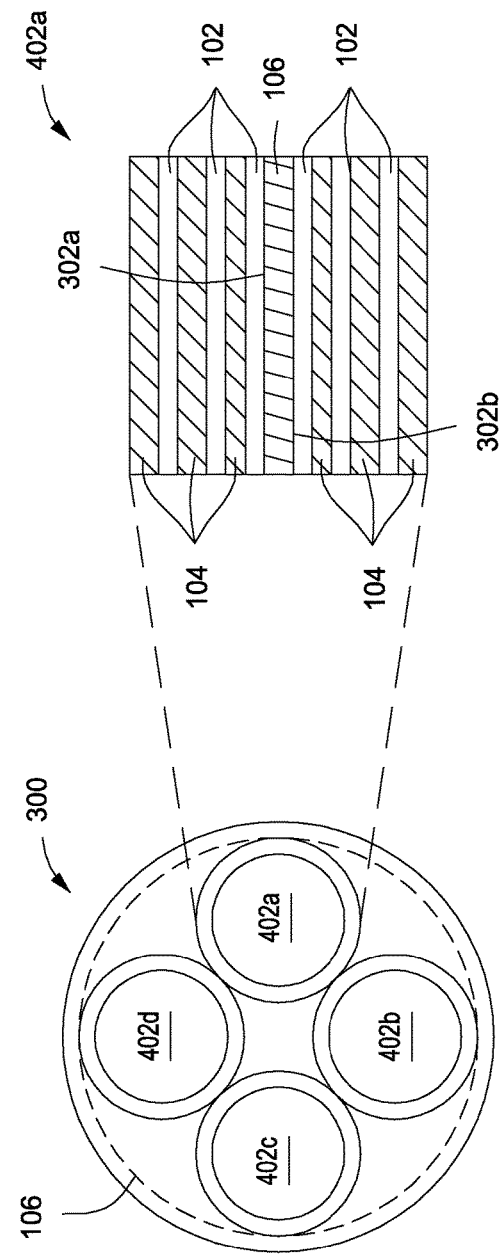
FIG. 4B
FIG. 4A

MANUFACTURING PROCESS FOR INTEGRATED COMPUTATIONAL ELEMENTS

BACKGROUND

The present disclosure is related to optical processing elements and, in particular, methods of manufacturing or fabricating an integrated computational element for use in an optical computing device.

Optical computing devices, also commonly referred to as "opticoanalytical devices," can be used to analyze and monitor a sample substance in real time. Such optical computing devices will often employ a light source that emits electromagnetic radiation that reflects from or is transmitted through the sample and optically interacts with an optical processing element to determine quantitative and/or qualitative values of one or more physical or chemical properties of the substance being analyzed. The optical processing element may be, for example, an integrated computational element (ICE). One type of an ICE is an optical thin film interference device, also known as a multivariate optical element (MOE). Each ICE can be designed to operate over a continuum of wavelengths in the electromagnetic spectrum from the UV to mid-infrared (MIR) ranges, or any sub-set of that region. Electromagnetic radiation that optically interacts with the sample substance is changed and processed by the ICE so as to be measured by a detector. The output of the detector can be correlated to a physical or chemical property of the substance being analyzed.

An ICE (hereafter "ICE core") typically includes a plurality of optical thin film layers consisting of various materials whose index of refraction and size (e.g., thickness) may vary between each layer. An ICE core design refers to the substrate, the number and thickness of the respective layers, and the refractive indices of each layer of the ICE core. The layers may be strategically deposited and sized so as to selectively pass predetermined fractions of electromagnetic radiation at different wavelengths configured to substantially mimic a regression vector corresponding to a particular physical or chemical property of interest of a substance of interest. Accordingly, an ICE core design will exhibit a transmission function that is weighted with respect to wavelength. As a result, the output light intensity from the ICE core conveyed to the detector may be related to the physical or chemical property of interest for the substance.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 3 illustrates a cross-sectional side view of an exemplary multilayer film stack device generated using atomic layer deposition, according to one or more embodiments.

FIG. 4A depicts a top view of the multilayer film stack device of FIG. 3, according to one or more embodiments.

FIG. 4B depicts a cross-sectional side view of an optical thin film unit excised or otherwise cut from the multilayer film stack device of FIG. 3, according to one or more embodiments.

DETAILED DESCRIPTION

Figure 1:
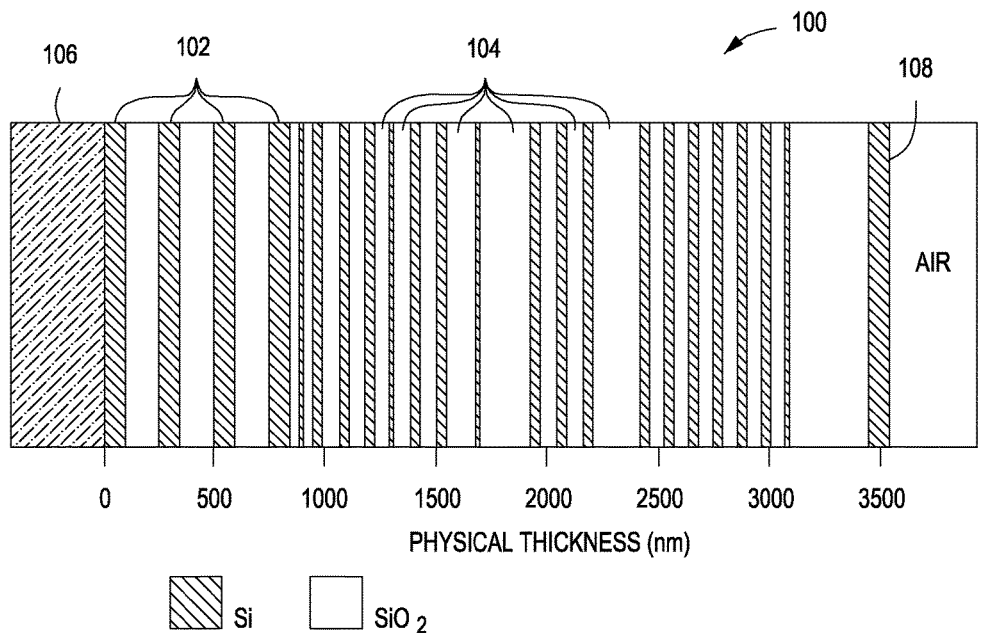
FIG. 1 illustrates an exemplary integrated computational element, according to one or more embodiments.

The present disclosure is related to optical processing elements and, in particular, methods of manufacturing or fabricating an integrated computational element for use in an optical computing device.

The present disclosure describes improved methods of manufacturing optical processing elements, such as integrated computational elements ("ICE cores"). In some embodiments, the several thin film layers that combine to make up an ICE core are deposited on opposing sides of a substrate during an atomic layer deposition (ALD) process. The resulting multilayer film stack device exhibits mirrored thin film layers on each planar side of the underlying substrate. The substrate may then be cleaved in two by making a planar cut or separation, and thereby rendering mirror ICE cores supported on at least a portion of the remaining substrate. The substrate may then be chemically or mechanically removed from the thin film layers, and the thin film layers can be subsequently draped over surfaces that would not have survived the thin film manufacturing process, or otherwise might have been inconvenient to coat using ALD techniques. Accordingly, the disclosed embodiments may prove advantageous in doubling the productivity of fabricating ICE cores during an ALD process and using the resulting ICE cores as a type of decal that can be selectively arranged on a target surface.

The present disclosure also describes building the several thin film layers of an ICE core on one side of a substrate supported on its opposing side on a support structure within a thin film deposition chamber. After suitably fabricating the ICE core, the substrate may then be chemically or mechanically removed from the thin film layers, and the thin film layers can be subsequently attached as a type of decal to a target surface that would not have survived the thin film manufacturing process.

The methods disclosed herein may be suitable for fabricating optical processing elements (e.g., ICE cores) for use in the oil and gas industry, such as for monitoring and detecting oil/gas-related substances (e.g., hydrocarbons, drilling fluids, completion fluids, treatment fluids, etc.). It will be appreciated, however, that the methods described herein are equally applicable to fabricating ICE cores for use in other technology fields including, but not limited to, the food industry, the paint industry, the mining industry, the agricultural industry, the medical and pharmaceutical industries, the automotive industry, the cosmetics industry, water treatment facilities, and any other field where it may be desired to monitor substances in real time.

As used herein, the term "characteristic" or "characteristic of interest" refers to a chemical, mechanical, or physical property of a substance or a sample of the substance. The characteristic of a substance may include a quantitative or qualitative value of one or more chemical constituents or compounds present therein or any physical property associated therewith. Such chemical constituents and compounds may be referred to herein as "analytes." Illustrative characteristics of a substance that can be analyzed with the help of the optical processing elements described herein can include, for example, chemical composition (e.g., identity and concentration in total or of individual components), phase presence (e.g., gas, oil, water, etc.), impurity content, pH, alkalinity, viscosity, density, ionic strength, total dissolved solids, salt content (e.g., salinity), porosity, opacity, bacteria content, total hardness, transmittance, state of matter (solid, liquid, gas, emulsion, mixtures thereof, etc.), and the like.

As used herein, the term "substance," or variations thereof, refers to at least a portion of matter or material of interest to be tested or otherwise evaluated with the help of the optical processing elements described herein. The substance may be any fluid capable of flowing, including particulate solids, liquids, gases (e.g., air, nitrogen, carbon dioxide, argon, helium, methane, ethane, butane, and other hydrocarbon gases, hydrogen sulfide, and combinations thereof), slurries, emulsions, powders, muds, glasses, mixtures, combinations thereof, and may include, but is not limited to, aqueous fluids (e.g., water, brines, etc.), non-aqueous fluids (e.g., organic compounds, hydrocarbons, oil, a refined component of oil, petrochemical products, and the like), acids, surfactants, biocides, bleaches, corrosion inhibitors, foamers and foaming agents, breakers, scavengers, stabilizers, clarifiers, detergents, treatment fluids, fracturing fluids, formation fluids, or any oilfield fluid, chemical, or substance commonly found in the oil and gas industry. The substance may also refer to solid materials such as, but not limited to, rock formations, concrete, solid wellbore surfaces, pipes or flow lines, and solid surfaces of any wellbore tool or projectile (e.g., balls, darts, plugs, etc.).

As used herein, the term "electromagnetic radiation" refers to radio waves, microwave radiation, terahertz, infrared and near-infrared radiation, visible light, ultraviolet light, X-ray radiation and gamma ray radiation.

As used herein, the term "optically interact" or variations thereof refers to the reflection, transmission, scattering, diffraction, or absorption of electromagnetic radiation either on, through, or from an optical processing element (e.g., an integrated computational element) or a substance being analyzed with the help of the optical processing element. Accordingly, optically interacted light refers to electromagnetic radiation that has been reflected, transmitted, scattered, diffracted, or absorbed by, emitted, or re-radiated, for example, using an optical processing element, but may also apply to optical interaction with a substance.

As used herein, the term "optical computing device" refers to an optical device that is configured to receive an input of electromagnetic radiation associated with a substance and produce an output of electromagnetic radiation from an optical processing element arranged within or otherwise associated with the optical computing device. The optical processing element may be, for example, an integrated computational element (ICE). The electromagnetic radiation that optically interacts with the optical processing element is changed so as to be readable by a detector, such that an output of the detector can be correlated to a particular characteristic of the substance being analyzed. The output of electromagnetic radiation from the optical processing element can be reflected, transmitted, and/or dispersed electromagnetic radiation. Whether the detector analyzes reflected, transmitted, or dispersed electromagnetic radiation may be dictated by the structural parameters of the optical computing device as well as other considerations known to those skilled in the art. In addition, emission and/or scattering of the fluid, for example via fluorescence, luminescence, Raman, Mie, and/or Raleigh scattering, can also be monitored by optical computing devices.

As indicated above, the present disclosure provides improved methods of manufacturing or fabricating optical processing elements, such as integrated computational elements (ICE cores), for use in optical computing devices. In operation, an ICE core is capable of distinguishing electromagnetic radiation related to a characteristic of interest of a substance from electromagnetic radiation related to other components of the substance.

Referring to FIG. 1, illustrated is an exemplary ICE core 100 that may be fabricated using the presently disclosed methods, according to one or more embodiments. As illustrated, the ICE core 100 may include a plurality of alternating thin film layers 102 and 104, such as silicon (Si) and $SiO_2$ (quartz), respectively. In general, these layers 102, 104 consist of materials whose index of refraction is high and low, respectively. Other examples of materials might include niobia and niobium, germanium and germania, MgF, SiO, $TiO_2$, $Al_2O_3$, and other high and low index materials known in the art. The layers 102, 104 may be strategically deposited on a substrate 106. In some embodiments, the substrate 106 is BK-7 optical glass. In other embodiments, the substrate 106 may be another type of optical substrate, such as another optical glass, silica, sapphire, silicon, germanium, zinc selenide, zinc sulfide, or various plastics such as polycarbonate, polymethylmethacrylate (PMMA), polyvinylchloride (PVC), diamond, ceramics, combinations thereof, and the like.

As will be described below, however, the substrate 106 may alternatively be made of a material that is cleavable in a single plane, and otherwise easily removed from the layers 102, 104 by physical or chemical means. For instance, the substrate 106 may be made of mica, pyrolitic carbon, graphite, or graphene.

At the opposite end (e.g., opposite the substrate 106 in FIG. 1), the ICE core 100 may include a layer 108 that is generally exposed to the environment of the device or installation, and may be able to detect a sample substance. The number of layers 102, 104 and the thickness of each layer 102, 104 are determined from the spectral attributes acquired from a spectroscopic analysis of a characteristic of the substance being analyzed using a conventional spectroscopic instrument. The spectrum of interest of a given characteristic typically includes any number of different wavelengths.

It should be understood that the ICE core 100 depicted in FIG. 1 does not in fact represent any particular ICE core configured to detect a specific characteristic of a given substance, but is provided for purposes of illustration only. Consequently, the number of layers 102, 104 and their relative thicknesses, as shown in FIG. 1, bear no correlation to any particular substance or characteristic thereof. Nor are the layers 102, 104 and their relative thicknesses necessarily drawn to scale, and therefore should not be considered limiting of the present disclosure.

In some embodiments, the material of each layer 102, 104 can be doped or two or more materials can be combined in a manner to achieve the desired optical characteristic. In addition to solids, the exemplary ICE core 100 may also contain liquids and/or gases, optionally in combination with solids, in order to produce a desired optical characteristic. In the case of gases and liquids, the ICE core 100 can contain a corresponding vessel (not shown), which houses the gases or liquids. Exemplary variations of the ICE core 100 may also include holographic optical elements, gratings, piezoelectric, light pipe, and/or acousto-optic elements, for example, that can create transmission, reflection, and/or absorptive properties of interest.

The multiple layers 102, 104 may exhibit different refractive indices. By properly selecting the materials of the layers 102, 104 and their relative thickness and spacing, the ICE core 100 may be configured to selectively transmit or reflect predetermined fractions of electromagnetic radiation at different wavelengths. Each wavelength is given a predetermined weighting or loading factor. The thickness and spacing of the layers 102, 104 may be determined using a variety of approximation methods from the spectrum of the characteristic or analyte of interest. These methods may include inverse Fourier transform (IFT) of the optical transmission spectrum and structuring the ICE core 100 as the physical representation of the IFT. The approximations convert the IFT into a structure based on known materials with constant refractive indices.

The weightings that the layers 102, 104 of the ICE core 100 apply at each wavelength are set to the regression weightings described with respect to a known equation, or data, or spectral signature. For instance, when electromagnetic radiation interacts with a substance, unique physical and chemical information about the substance is encoded in the electromagnetic radiation that is reflected from, transmitted through, or radiated from the substance. This information is often referred to as the spectral "fingerprint" of the substance. The ICE core 100 may be configured to perform the dot product of the received electromagnetic radiation and the wavelength dependent transmission function of the ICE core 100. The wavelength dependent transmission function of the ICE core 100 is dependent on the material refractive index of each layer, the number of layers 102, 104 and thickness of each layer 102, 104. As a result, the output light intensity of the ICE core 100 is related to the characteristic or analyte of interest.

As further explanation, accurately determining the regression vector of the characteristic of interest in the sample substance provides a means for an optical computing device to determine or otherwise calculate a concentration of said characteristic in the sample substance. The regression vector for each characteristic may be determined using standard procedures that will be familiar to one having ordinary skill in the art. For example, analyzing the spectrum of the sample substance may include determining a dot product of the regression vector for each characteristic of the sample substance being analyzed. As one of ordinary skill in art will recognize, a dot product of a vector is a scalar quantity (i.e., a real number). While the dot product value is believed to have no physical meaning by itself (e.g., it may return a positive or negative result of any magnitude), comparison of the dot product value of a sample substance with dot product values obtained for known reference standards and plotted in a calibration curve may allow the sample substance dot product value to be correlated with a concentration or value of a characteristic, thereby allowing unknown sample substances to be accurately analyzed.

To determine the dot product, one simply multiples the regression coefficient of the regression vector at a given wavelength by the spectral intensity at the same wavelength. This process is repeated for all wavelengths analyzed, and the products are summed over the entire wavelength range to yield the dot product. Those skilled in the art will recognize that two or more characteristics may be determined from a single spectrum of the sample substance by applying a corresponding regression vector for each characteristic.

In practice, it is possible to derive information from electromagnetic radiation interacting with a sample substance by, for example, separating the electromagnetic radiation from several samples into wavelength bands and performing a multiple linear regression of the band intensity against a characteristic of interest determined by another measurement technique for each sample substance. The measured characteristic may be expressed and modeled by multiple linear regression techniques that will be familiar to one having ordinary skill in the art. Specifically, if y is the measured value of the concentration or characteristic, y may be expressed as in Equation 1:

$$y = a_0 + a_1 w_1 + a_2 w_2 + a_3 w_3 + a_4 w_4 + \ldots \qquad \text{Equation (1)}$$

where each 'a' is a constant determined by the regression analysis and each 'w' is the light intensity for each wavelength band. Depending on the circumstances, the estimate obtained from Equation (1) may be inaccurate, for example, due to the presence of other characteristics within the sample substance that may affect the intensity of the wavelength bands. A more accurate estimate may be obtained by expressing the electromagnetic radiation in terms of its principal components.

To obtain the principal components, spectroscopic data is collected for a variety of similar sample substances using the same type of electromagnetic radiation. For example, following exposure to each sample substance, the electromagnetic radiation may be collected and the spectral intensity at each wavelength may be measured for each sample substance. This data may then be pooled and subjected to a linear-algebraic process known as singular value decomposition (SVD) in order to determine the principal components. Use of SVD in principal component analysis will be well understood by one having ordinary skill in the art. Briefly, however, principal component analysis is a dimension reduction technique that takes 'm' spectra with 'n' independent variables and constructs a new set of eigenvectors that are linear combinations of the original variables. The eigenvectors may be considered a new set of plotting axes. The primary axis, termed the first principal component, is the vector that describes most of the data variability. Subsequent principal components describe successively less sample variability, until the higher order principal components essentially describe only spectral noise.

Typically, the principal components are determined as normalized vectors. Thus, each component of an electromagnetic radiation sample may be expressed as $x_n z_n$, where $x_n$ is a scalar multiplier and $z_n$ is the normalized component vector for the $n^{th}$ component. That is, $z_n$ is a vector in a multi-dimensional space where each wavelength is a dimension. Normalization determines values for a component at each wavelength so that the component maintains its shape and the length of the principal component vector is equal to one. Thus, each normalized component vector has a shape and a magnitude so that the components may be used as the basic building blocks of any electromagnetic radiation sample having those principal components. Accordingly, each electromagnetic radiation sample may be described by a combination of the normalized principal components multiplied by the appropriate scalar multipliers, as set forth in Equation (2):

$$x_1 z_1 + x_2 z_2 + \ldots + x_n z_n \qquad \text{Equation (2)}$$

The scalar multipliers $x_n$ may be considered the "magnitudes" of the principal components in a given electromagnetic radiation sample when the principal components are understood to have a standardized magnitude as provided by normalization.

Because the principal components are orthogonal, they may be used in a relatively straightforward mathematical procedure to decompose an electromagnetic radiation sample into the component magnitudes, which may accurately describe the data in the original electromagnetic radiation sample. Since the original electromagnetic radiation sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Because the principal components are orthogonal to each other, the dot product of any principal component with any other principal component is zero. Physically, this means that the components do not interfere with each other. If data is altered to change the magnitude of one component in the original electromagnetic radiation signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the electromagnetic radiation samples. Thus, in a mathematical sense, the principal components are components of the original electromagnetic radiation that do not interfere with each other and that represent the most compact description of the spectral signal. Physically, each principal component is an electromagnetic radiation signal that forms a part of the original electromagnetic radiation signal. Each principal component has a shape over some wavelength range within the original wavelength range. Summing the principal components may produce the original signal, provided each component has the proper magnitude, whether positive or negative.

The principal components may comprise a compression of the information carried by the total light signal. In a physical sense, the shape and wavelength range of the principal components describe what information is in the total electromagnetic radiation signal, and the magnitude of each component describes how much of that information is present. If several electromagnetic radiation samples contain the same types of information, but in differing amounts, then a single set of principal components may be used to describe (except for noise) each electromagnetic radiation sample by applying appropriate magnitudes to the components. The principal components may be used to provide an estimate of the characteristic of the sample substance based upon the information carried by the electromagnetic radiation that has interacted with that sample substance. Differences observed in spectra of sample substances having varying quantities of an analyte or values of a characteristic may be described as differences in the magnitudes of the principal components. Thus, the concentration of the characteristic may be expressed by the principal components according to Equation (3) in the case where four principal components are used:

$$y=a_0+a_1x_1+a_2x_2+a_3x_3+a_4x_4 \quad \text{Equation (3)}$$

where 'y' is a concentration or value of a characteristic, each a is a constant determined by the regression analysis, and $x_1$, $x_2$, $x_3$ and $x_4$ are the first, second, third, and fourth principal component magnitudes, respectively. Equation (3) may be referred to as a regression vector. The regression vector may be used to provide an estimate for the concentration or value of the characteristic for an unknown sample.

Regression vector calculations may be performed by computer, based on spectrograph measurements of electromagnetic radiation by wavelength. The spectrograph system spreads the electromagnetic radiation into its spectrum and measures the spectral intensity at each wavelength over the wavelength range. Using Equation (3), the computer may read the intensity data and decompose the electromagnetic radiation sample into the principal component magnitudes $x_n$ by determining the dot product of the total signal with each component. The component magnitudes are then applied to the regression equation to determine a concentration or value of the characteristic.

To simplify the foregoing procedure, however, the regression vector may be converted to a form that is a function of wavelength so that only one dot product is determined. Each normalized principal component vector $z_n$ has a value over all or part of the total wavelength range. If each wavelength value of each component vector is multiplied by the regression constant and corresponding to the component vector, and if the resulting weighted principal components are summed by wavelength, the regression vector takes the form of Equation (4):

$$y=a_0+b_1u_1+b_2u_2+\ldots+b_nu_n \quad \text{Equation (4)}$$

where $a_0$ is the first regression constant from Equation (3), $b_n$ is the sum of the multiple of each regression constant $a_n$ from Equation (3) and the value of its respective normalized regression vector at wavelength 'n', and $u_n$ is the intensity of the electromagnetic radiation at wavelength 'n'. Thus, the new constants define a vector in wavelength space that directly describes a concentration or characteristic of a sample substance. The regression vector in the form of Equation (4) represents the dot product of an electromagnetic radiation sample with this vector.

Normalization of the principal components provides the components with an arbitrary value for use during the regression analysis. Accordingly, it is very unlikely that the dot product value produced by the regression vector will be equal to the actual concentration or characteristic value of a sample substance being analyzed. The dot product result is, however, proportional to the concentration or characteristic value. As discussed above, the proportionality factor may be determined by measuring one or more known calibration samples by conventional means and comparing the result to the dot product value of the regression vector. Thereafter, the dot product result can be compared to the value obtained from the calibration standards in order to determine the concentration or characteristic of an unknown sample being analyzed.

Figure 2:
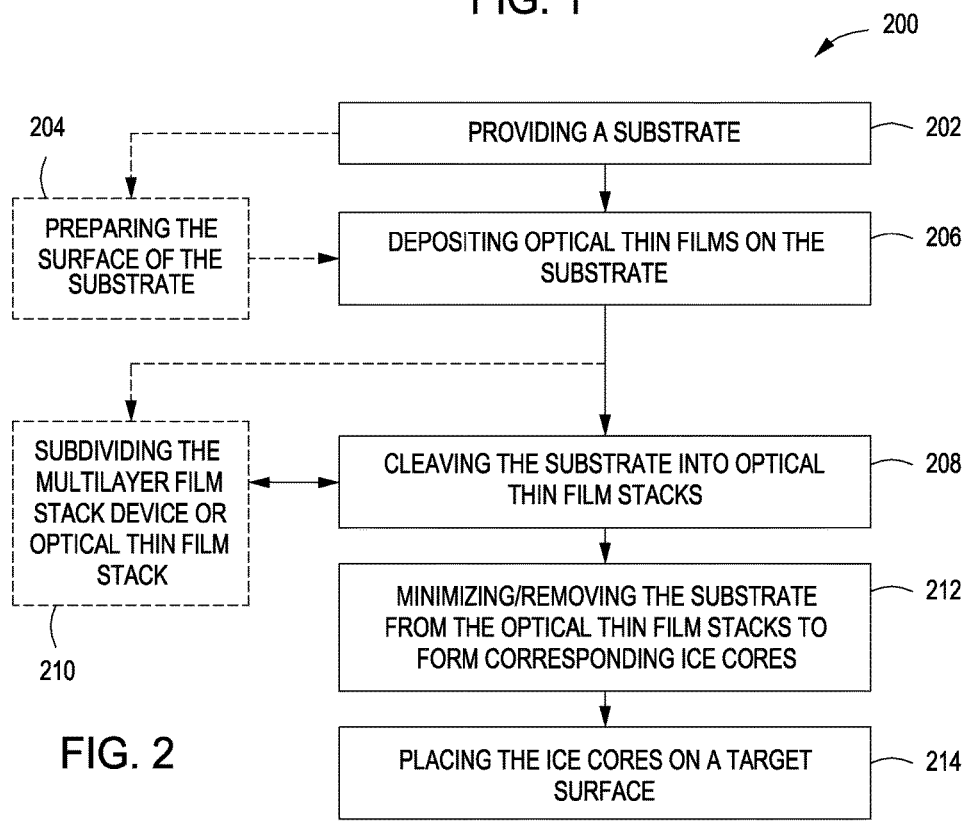
FIG. 2 depicts a schematic flowchart of an exemplary method of manufacturing an optical processing element, according to one or more embodiments.

Referring now to FIG. 2, with continued reference to FIG. 1, illustrated is a schematic flowchart of an exemplary method 200 of manufacturing an optical processing element, according to one or more embodiments. Optical processing elements that result from following the method 200 may be substantially similar to the ICE core 100 of FIG. 1, and otherwise useful in analyzing a sample substance for an analyte or characteristic of interest associated with the sample substance.

According to the method 200, a substrate for the optical processing element may first be provided, as at 202. A suitable substrate may be similar to the substrate 106 described above with reference to FIG. 1. Preferably, the substrate exhibits optical properties that are compliant with the optical bandwidth of interest (i.e., significantly flat and high % transmission profile). Suitable substrate materials also include those that exhibit a physical stability sufficient to withstand elevated temperatures and extreme conditions typically associated with thin film deposition processes and techniques.

In at least one embodiment, the substrate may be generally disc-shaped and therefore include a first surface and a second surface that is opposite or substantially opposite the first surface. In embodiments where the first and second surfaces are substantially opposite one another, the first and second surfaces may be planar surfaces that are parallel to one another or slightly offset from parallel, without departing from the scope of the disclosure.

In some embodiments, the substrate may be made of a material that is cleavable in a single plane, such that it may be subsequently cleaved in plane or otherwise removed from the optical processing element using mechanical means. In other embodiments, the substrate may be made of a material that may be removed from the optical processing element using chemical means. In yet other embodiments, the substrate may be made of a material that can be removed from the optical processing element using both mechanical and chemical means. Suitable materials for the substrate include, but are not limited to, mica, pyrolitic carbon, graphite, graphene, and any other materials that exhibit substantially similar chemical compositions or atomic structures. In at least one embodiment, the substrate may be a salt (i.e., NaCl) that is polished and then subsequently flash-coated with aluminum to get the desire reactive surface for a substrate. In yet other embodiments, the substrate may be a plastic, such as polyethylene terephthalate (PET), or one or more cellulose films.

In some embodiments, the method 200 may include preparing the surface of the substrate, as at 204. Preparing the surface of the substrate may include reducing the thickness of the substrate until a desired or predetermined thickness of the substrate is achieved. In some embodiments, the thickness of the substrate may be reduced through chemical means, such as etching or oxidation. In other embodiment, however, especially in embodiments where the substrate is graphite, the thickness of the substrate may be sequentially reduced by cleaving the surface of the substrate and thereby producing individual layers or sheets of graphene. In at least one embodiment, the graphene sheets may be used as a suitable substrate, for example. Accordingly, the substrate may exhibit a very small thickness, such as in the range of a few angstroms.

In other embodiments, preparing the surface of the substrate may include chemically treating the surface of the substrate so that it becomes more amenable or receptive to a particular thin film deposition process. For instance, in the case where atomic layer deposition (ALD) is used, the ALD process can be surface selective. In other words, some of the materials used to build the layers (i.e., layers 102, 104 of FIG. 1) of the optical processing element may not chemically bond or otherwise adhere to the given substrate. To accommodate layer chemistries that may not directly adhere to the given substrate, the surface of the substrate may be coated or otherwise pre-treated with a reactive agent, such as aluminum, titanium, silicon, germanium, indium, gallium, and arsenic. This may be done using sputtering techniques known to those skilled in the art. The reactive agent may then be reacted in order to generate an oxide surface that may be more responsive to ALD techniques. In other embodiments, the surface of the substrate may be treated with an oxidation product, without departing from the scope of the disclosure.

Once the surface of the substrate is properly or suitably prepared, multiple optical thin films may be deposited on the substrate via a thin film deposition process to generate a multilayer film stack device, as at 206. In the present embodiment, the thin film deposition process may be an ALD process, such as those generally known to those skilled in the art. In embodiments discussed below, however, the thin film deposition process may be any chemical or physical thin film deposition technique known to those skilled in the art including, but not limited to, plating, chemical solution deposition, spin coating, chemical vapor deposition, plasma enhanced chemical vapor deposition, physical vapor deposition, sputtering, pulsed laser deposition, cathodic arc deposition, electrohydrodynamic deposition (i.e., electrospray deposition), and ion-assisted e-beam deposition.

In the present embodiment, subjecting the substrate to an ALD process, as at 206, may include introducing the substrate into an ALD reaction chamber. The substrate may be hung or suspended within the ALD reaction chamber such that both planar sides of the substrate may be evenly coated during each stage of the deposition process. In at least one embodiment, in order to properly suspend the substrate within the ALD reaction chamber, the substrate may be secured to a clip or other support structure associated with the ALD reaction chamber.

Once the substrate is suitably arranged (i.e., hung) within the ALD reaction chamber, the ALD process may then proceed to sequentially (i.e., consecutively) grow the various layers (i.e., layers 102, 104 of FIG. 1) on the substrate. Briefly, this process includes introducing a first gaseous compound or "precursor" into the ALD reaction chamber to chemically bond to the substrate; purging or evacuating the ALD reaction chamber to remove any non-reacted precursors and/or gaseous reaction by-products; introducing a second precursor into the ALD reaction chamber to chemically react to the substrate bonded precursor of the previous cycle to form a monolayer; purging or evacuating the ALD reaction chamber to remove any non-reacted precursors and/or gaseous reaction by-products of the second precursor; and repeating the foregoing steps as many times as required for the desired number of layers and the desired thickness of each layer.

Due to self-terminating reactions inherent in ALD processing, ALD is characterized as a surface-controlled process, where the predominant process parameters of control include the precursors (and their flow rates), the substrate, and the ambient temperature inside the ALD reaction chamber. Moreover, because of the surface control that is inherent in ALD processes, the resulting layers deposited on the substrate are extremely conformal and otherwise uniform in thickness on each side of the substrate.

Referring briefly to FIG. 3, with continued reference to FIG. 2, illustrated is a cross-sectional side view of an exemplary multilayer film stack device 300 that may be generated using the foregoing ALD process, according to one or more embodiments. As depicted in FIG. 3, the substrate 106 is encased and otherwise entirely covered with a plurality of alternating thin film layers 102 and 104, similar to those described above with reference to FIG. 1. It is noted that the number of layers 102, 104 and their relative thicknesses, as depicted in FIG. 3, are not drawn to scale, and therefore should not be considered limiting of the present disclosure.

Notably, the layers 102, 104 are depicted as being deposited uniformly on all sides of the substrate 106. More particularly, the substrate 106 has first and second surfaces 302a and 302b, respectively, and the layers 102, 104 are built up or "grown" uniformly on each surface 302a,b. Accordingly, the multilayer film stack device 300 exhibits layers 102, 104 that are mirrored on each surface 302a,b.

In at least one embodiment, the initial or first layer 102 deposited on the substrate may be made of a metal oxide material, such as aluminum oxide ($Al_2O_3$) or titanium dioxide ($TiO_2$). As will be appreciated, the oxide material of the first layer 102 may prove advantageous in creating a good adhesion to the substrate 106, and thereby protecting the thin films from inadvertent removal from the substrate 106. In some embodiments, one or both of the first and last layers 102, 104 of the multilayer film stack device 300 may be deposited to a thickness that is greater than the other interposing layers 102, 104. As will be appreciated, providing thicker first and/or last layers 102, 104 may provide greater core mechanical strength to the multilayer film stack device 300, thereby resulting in a more robust multilayer film stack device 300.

Referring again to FIG. 2, the method 200 may also include cleaving the substrate to produce at least two mirror optical thin film stacks, as at 208. Those skilled in the art will readily recognize that there are multiple ways to cleave the substrate. In one embodiment, for example, the optical thin film stack can be cleaved in two by making a planar cut through the substrate. This can be done with a laser or a focused ion beam, for example. In other embodiments, the substrate may be mechanically separated, such as through the application of a shear load across the substrate that results in the substrate shearing along an atomic layer associated therewith. Advantageously, since the substrate is made from a cleavable material that is shearable along a crystallographic axis, cleaving the substrate mechanically may not compromise the integrity of the mirror optical thin film stacks.

In yet other embodiments, one or more additional layers may be deposited on the substrate that exhibit different thermal expansion coefficients than the other thin film layers in the plane of deposition. Upon the multilayer film stack device assuming a large temperature change, the substrate may separate along the layers of dissimilar thermal expansion coefficients. In some embodiments, for example, this may be accomplished by depositing layers of aluminum inter-digited (e.g., alternating) with one or more layers of iron oxides. Such alternating layers may prove advantageous in generating a thermal reaction that causes the substrate to separate.

In some embodiments, prior to or after cleaving the substrate, the method 200 may include subdividing the multilayer film stack device/stacks into multiple smaller optical thin film units, as at 210. Accordingly, in some embodiments, the multilayer film stack device 300 of FIG. 3 may be subdivided into multiple smaller optical thin film units prior to cleaving the underlying substrate 106. In other embodiments, however, after cleaving the substrate 106 of the multilayer film stack device 300 to produce the mirror optical thin film stacks, as at 208 above, each resulting optical thin film stack may be subdivided into multiple smaller optical thin film units.

Referring to FIGS. 4A and 4B, with continued reference to FIG. 3, illustrated are views of the multilayer film stack device 300, according to one or more embodiments. More particularly, FIG. 4A depicts a top view of the multilayer film stack device 300, and FIG. 4B depicts a cross-sectional side view of an optical thin film unit excised or otherwise cut from the multilayer film stack device 300.

As illustrated In FIG. 4A, the substrate 106 used to support the several optical thin film layers 102, 104 is generally circular, thereby resulting in a generally circular multilayer film stack device 300. The multilayer film stack device 300 is depicted as having been subdivided (e.g., diced, partitioned, apportioned, etc.) into four optical thin film units 402 (shown as optical thin film units 402a, 402b, 402c, and 402d. Subdividing the multilayer film stack device 300 into multiple optical thin film units 402a-d may be accomplished by various thin film dicing techniques known to those skilled in the art, such as laser dicing.

Each optical thin film unit 402a-d includes a portion of the substrate 106 and, similar to the multilayer film stack device 300 depicted in FIG. 3, each optical thin film unit 402a-d includes mirrored stacks of layers 102, 104 built up or grown uniformly on each surface 302a,b of the substrate 106. FIG. 4B depicts a cross-sectional side view of the first optical thin film unit 402a, but it will be appreciated that the other optical thin film units 402b-d would be substantially similar in structure. It will also be appreciated that, while only four optical thin film units 402a-d are depicted in FIG. 4A, the multilayer film stack device 300 may be diced into more or less than four optical thin film units 402a-d, without departing from the scope of the disclosure. The number of optical thin film units will depend primarily on the size of the substrate 106 and the desired size of the resulting optical processing elements.

Referring again to FIG. 2, once the optical thin film units are successfully diced or otherwise subdivided from the multilayer film stack device, the substrate from each optical thin film unit may then be cleaved, as at 208, and as generally described above. Cleaving the optical thin film units at the substrate will result in corresponding optical thin film stacks having a portion of the substrate remaining thereon.

The method 200 may then include removing the remaining portions of the substrate from the optical thin film stacks, as at 212, thereby resulting in corresponding stacks of optical thin films that can be used as ICE cores, as generally described above. It should be noted that "removing" the substrate from the optical thin film stack also includes minimizing the thickness of the substrate and otherwise not entirely removing every remnant of the substrate from the optical thin films. Accordingly, the terms "removing" and "minimizing" are used interchangeably herein, but will generally be discussed in terms of "removing" the substrate.

The substrate can be removed from the optical thin film stacks either chemically or mechanically. In removing the substrate chemically, layers of the substrate may be removed by subjecting the substrate to low temperature oxidation. In other embodiments, layers of the substrate may be removed by subjecting the substrate to elevated temperature oxidation, such as exposing the substrate to oxygen ($O_2$) or ozone ($O_3$) and thereby combusting the substrate. In yet other embodiments, the substrate may be removed by placing the optical thin film stack in a solvent bath and allowing a solvent to react with and otherwise etch or dissolve the substrate. Contamination may be controlled by processing the substrates at reduced pressures.

In removing the substrate mechanically, layers of the substrate may be removed sequentially using shear forces applied tangentially against the substrate. In other embodiments, especially in the case of graphite, conventional adhesive tape may be used to sequentially or systematically remove atomic layers of graphite (i.e., graphene layers) until a desired thickness of the substrate remains or the substrate is removed altogether from the first layer. In yet other embodiments, the optical thin films may be pliable or bendable such that when the optical thin film stack is bent slightly with a mechanical force applied on opposing sides of the stack, the substrate is able to "pop off" the first layer or is otherwise forcibly removed from the optical thin film stack. Such may be the case when the substrate material is mica, for example.

It should be noted that the substrate could be removed prior to (or in place of) cleaving the substrate. Accordingly, in at least one embodiment, steps 210 and 212 of the method 200 may be reversed, without departing from the scope of the disclosure. In such cases, the chemical or mechanical methods of removing the substrate may also result in cleaving the substrate, as at 208, such that the corresponding optical thin film stacks result.

In some embodiments, the method 200 may further include placing the ICE cores on a target surface, as at 214. More particularly, the ICE cores resulting from cleaving and/or subdividing the multilayer film stack device may be attached or otherwise adhered to a secondary optical element that either would not have survived the ALD process (or other thin film deposition processes) or would be impractical to place in the ALD reaction chamber. The secondary optical element may be any optical element, device, mechanism, or component that may be used in the optical computing devices described herein, and the ICE core may operate therewith in order to determine analytes of interest of a sample substance. For example, the secondary optical element may be, but is not limited to, a sector of a filter wheel, a band pass filter, a lens, a surface of an optical fiber, a sampling window, a sapphire optical element, a non-planar optical element (e.g., the surface of a lamp, light bulb, or other source of electromagnetic radiation), and a detector.

In some embodiments, the ICE cores may be manually placed on the secondary optical element. This may be accomplished by hand or with the help of a tool or device, such as pliers, tweezers, or the like. In embodiments where the substrate is graphite and at least a portion of the graphite substrate remains on a given ICE core, magnetic tweezers may be used to manipulate the position of the given ICE core. As known in the art, graphite is a diamagnetic material that generally creates a magnetic field in opposition of an applied magnetic field. Accordingly, magnetic tweezers may be used to capture and levitate the given ICE core between the opposing magnets of the tweezers. The given ICE core may then be brought to a target surface of the secondary optical element and appropriately arranged thereon.

An adhesive may be used to secure the ICE core to the target surface. In at least one embodiment, the magnetic tweezers (or another magnet) may be used to apply a magnetic clamping or pinning force on the ICE core against the target surface until the adhesive properly sets. The magnetic repulsion effected on the graphite portion of the ICE core by the magnet may serve to maintain the ICE core securely seated on the target surface. Suitable adhesives include any optically transparent adhesive, or any adhesive that exhibits little to no spectral features. In some embodiments, however, the adhesive could also be applied about the periphery of the ICE core (as opposed to its central locations) so that light passing through the ICE core and the secondary optical element is not adversely affected by the adhesive. Once the adhesive dries, the magnetic clamping force may be removed from the ICE core and, if desired, the remaining portions of the substrate may be chemically etched or otherwise removed from the optical thin film layers.

In other embodiments, the ICE core may be bonded or otherwise attached to the secondary optical element at the target surface using known sintering, welding, or bonding techniques. Such bonding techniques may include, but are not limited to low temperature glass frit bonding, glass soldering, seal glass bonding, pressure bonding, and wafer bonding. In such embodiments, the edges of the ICE core may be sintered to the target surface. In embodiments where the target surface is made of a low temperature melting glass or plastic, the target surface may be partially melted in order to securely bond the ICE core to the secondary optical element.

In yet other embodiments, the remaining portions of the substrate on the ICE core may be chemically etched or otherwise reacted in order to form a proper adhesion to the secondary optical element. More specifically, a magnet or other magnetic device (i.e., magnetic tweezers, etc.) may be used to push or otherwise pin the ICE core against the target surface while the substrate is chemically etched or reacted. Upon chemically reacting the substrate with oxygen ($O_2$) or ozone ($O_3$), for example, the resulting combustion process may serve to partially melt a plastic or glass target surface of the secondary optical element and thereby bond the ICE core thereto.

Placing the ICE cores on the target surface, as at 214, may also be accomplished in a solvent bath. More particularly, in embodiments where the substrate is removed chemically in a solvent bath, as at 212, the ICE cores may be floating in the solvent bath following dissolution or etching of the substrate. In such cases, a secondary optical element may be manipulated up through or otherwise within the solvent bath to capture the given ICE core using surface tension forces. The given ICE core may engage the secondary optical element at the target location and drape itself over its surface. In other embodiments, the secondary optical element may be disposed within the solvent bath and the solvent may be drained to allow the ICE core to land on and drape over the secondary optical element at the target location. Once the solvent dries, the ICE core may form a permanent part of the secondary optical element. In some embodiments, however, the ICE core may be sintered, welded, or bonded to the target surface, as generally described above, without departing from the scope of the disclosure.

Figure 5:
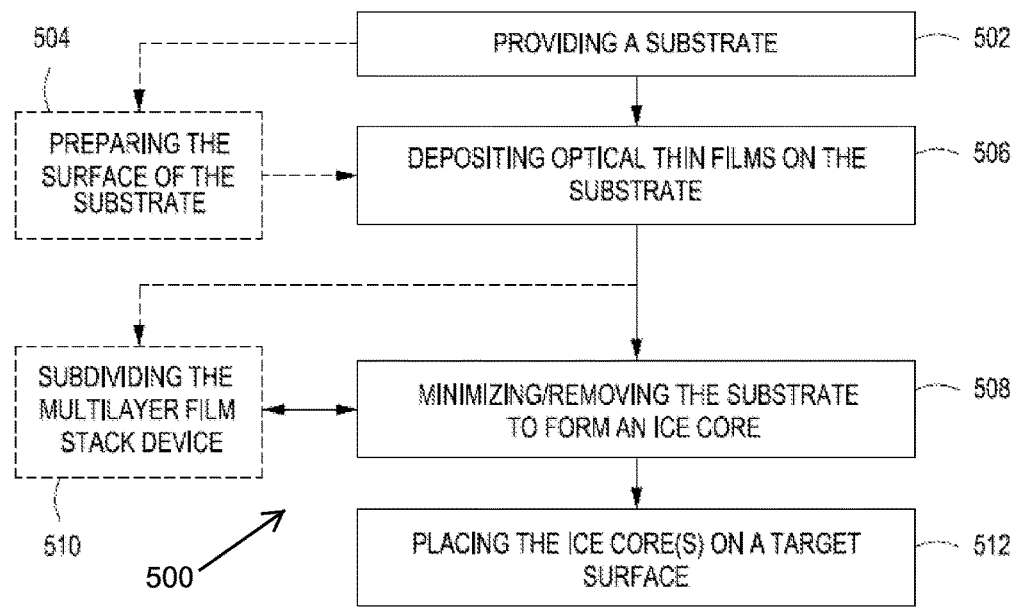
FIG. 5 depicts a schematic flowchart of another exemplary method of manufacturing an optical processing element, according to one or more embodiments.

Referring now to FIG. 5, illustrated is a schematic flowchart of another exemplary method 500 of manufacturing an optical processing element, according to one or more embodiments. The method 500 may be similar in some respects to the method 200 of FIG. 2 and therefore may be best understood with reference thereto, where like elements or steps from method 200 are not described again in detail below. Similar to the method 200 of FIG. 2, optical processing elements that result from following the method 500 may be substantially similar to the ICE core 100 of FIG. 1, and otherwise useful in analyzing a sample substance for an analyte or characteristic of interest associated with the sample substance.

According to the method 500, a substrate for the optical processing element may first be provided, as at 502. Again, suitable substrates may be made of a material that is cleavable in a single plane and/or a material that may be removed from the optical processing element using chemical means. Suitable substrate materials also include those that are able to withstand elevated temperatures that are typically associated with thin film deposition processes and techniques. Suitable materials for the substrate include, but are not limited to, mica, pyrolitic carbon, graphite, graphene, and any other materials that exhibit substantially similar chemical compositions or atomic structures.

In some embodiments, the method 500 may include preparing the surface of the substrate, as at 504, and similar to 202 of the method 200. As discussed above, preparing the surface of the substrate may include chemically or mechanically reducing the thickness of the substrate until a desired or predetermined thickness of the substrate is achieved. Preparing the surface of the substrate may also include chemically treating the surface of the substrate so that it becomes more amenable or receptive to a particular thin film deposition process.

Once the surface of the substrate is properly or suitably prepared, multiple optical thin films may be deposited on the substrate via a thin film deposition process, as at 506, and thereby generating a multilayer film stack device. In the present embodiment of method 500, the thin film deposition process is not limited to an ALD process, but rather includes any chemical or physical thin film deposition technique known to those skilled in the art including, but not limited to, plating, chemical solution deposition, spin coating, chemical vapor deposition, plasma enhanced chemical vapor deposition, physical vapor deposition, sputtering, pulsed laser deposition, cathodic arc deposition, electrohydrodynamic deposition (i.e., electrospray deposition), and ion-assisted e-beam deposition.

Depositing the multiple optical thin films on the substrate may include introducing the substrate into a reaction chamber and arranging the substrate on a support structure within the reaction chamber such that one surface of the substrate is exposed to the environment of the reaction chamber. During the deposition process, the exposed surface of the substrate will have the optical thin films sequentially (i.e., consecutively) deposited thereon. As with the embodiments of method 200, any number of optical thin film layers exhibiting any desired thickness may be deposited on the substrate. Moreover, in at least one embodiment, the initial or first layer deposited on the substrate may be made of a metal oxide material, such as aluminum oxide ($Al_2O_3$) or titanium dioxide ($TiO_2$), in order to create a suitable adhesion to the substrate, and thereby protecting the deposited optical thin films from inadvertent removal from the substrate. The first and/or final optical thin film layers may also be deposited to a thickness generally greater than the interposing optical thin film layers, and thereby generating a more robust multilayer film stack device.

After the optical thin film layers are deposited on the substrate and the multilayer film stack device is produced, as at 506, the method 500 may include removing the substrate from the multilayer film stack device, as at 508, and thereby providing a stack of optical thin films that can be used as an ICE core, as generally described above. Again, it is noted that "removing" the substrate from the optical thin film stack also includes minimizing the thickness of the substrate and otherwise not entirely removing every remnant of the substrate from the optical thin films. Accordingly, the term "removing" is used herein to denote minimizing the substrate or removing it altogether from the optical thin films.

As with the embodiments of method 200, the substrate can be removed from the optical thin film stack either chemically or mechanically. In removing the substrate chemically, layers of the substrate may be removed by subjecting the substrate to low temperature oxidation, exposing the substrate to oxygen ($O_2$) or ozone ($O_3$), and/or placing the optical thin film stack in a solvent bath and allowing a solvent to etch or dissolve the substrate. In removing the substrate mechanically, layers of the substrate may be removed sequentially using shear forces applied tangentially against the substrate or, as in the case of graphite, conventional adhesive tape may be used to sequentially remove atomic layers of graphite (i.e., graphene layers) until a desired thickness (including no thickness) of the substrate remains. In yet other embodiments, the optical thin films may be pliable such that when the optical thin film stack is bent, the substrate is able to "pop off" the first layer or is otherwise forcibly removed from the optical thin film stack. Such may be the case when the substrate material is mica, for example.

The method 500 may further include subdividing the optical thin film stack into multiple smaller optical thin film stacks, as at 510, whereby each smaller optical thin film stack may be used as an ICE core. As will be appreciated, however, subdividing the optical thin film stack may equally be performed prior to removing the substrate from the multilayer film stack device, as at 508, and thereby generating multiple smaller optical thin film stacks having a portion of the substrate remaining thereon. Accordingly, in at least one embodiment, steps 508 and 510 of the method 500 may be reversed, without departing from the scope of the disclosure.

The method 500 may further include placing the ICE core(s) on a target surface, as at 512. Placing the ICE core(s) on a target surface may include attaching or otherwise adhering the ICE core(s) to a secondary optical element that either would not have survived the thin film deposition process or would otherwise have been impractical to place in the thin film reaction chamber. The secondary optical element is defined above, and therefore will not be described again in detail.

Similar to step 214 of the method 200 of FIG. 2, the ICE core(s) may be manually placed on the secondary optical element, such as by hand or otherwise through the use of a tool or device. The ICE core(s) may also be placed on the target surface while floating in a solvent bath, such as by capturing a given ICE core using surface tension forces while the ICE core floats in the solvent bath, or draining the fluids from the solvent bath such that the given ICE core lands on and drapes itself over the secondary optical element at a target surface. Once the solvent dries, the ICE core may be attached to the secondary optical element. In other embodiments, however, the ICE core may be bonded or otherwise attached to the secondary optical element at the target surface using known sintering, welding, or bonding techniques.

In some embodiments, an adhesive may be used to secure the ICE core(s) to the target surface. The adhesive may be optically transparent or otherwise applied about the periphery of the ICE core (as opposed to its central locations) so that light passing through the ICE core and the secondary optical element is not adversely affected by the adhesive. Once the adhesive dries, the ICE core(s) may be effectively bonded to the secondary optical element. In some embodiments, the remaining portions of the substrate (if any) may then be chemically etched or otherwise removed from the optical thin film layers. In other embodiments, the ICE core(s) may be bonded or otherwise attached to the secondary optical element at the target surface using known sintering, welding, or bonding techniques. In yet other embodiments, any remaining portions of the substrate on the ICE core(s) may be chemically etched or otherwise reacted in order to melt portions of the underlying target surface or the ICE core and thereby form a proper adhesion to the secondary optical element.

Figure 6:
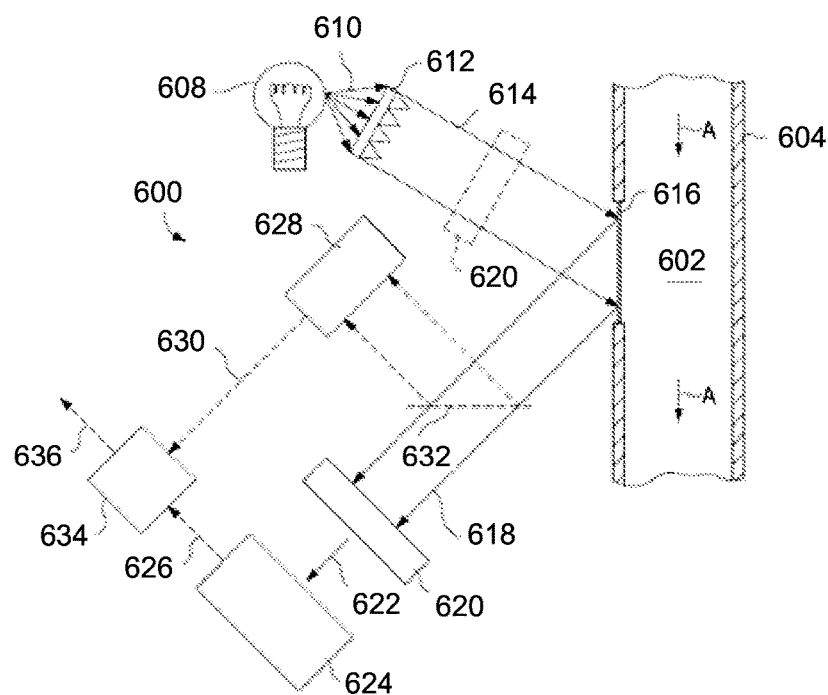
FIG. 6 illustrates an exemplary optical computing device for monitoring a sample substance, according to one or more embodiments.

Referring now to FIG. 6, illustrated is an exemplary optical computing device 600 for monitoring a sample substance 602, according to one or more embodiments. In the illustrated embodiment, the sample substance 602 may be contained or otherwise flowing within an exemplary flow path 604. The flow path 604 may be a flow line, a pipeline, a wellbore, an annulus defined within a wellbore, or any flow lines or pipelines extending to/from a wellbore. The sample substance 602 present within the flow path 604 may be flowing in the general direction indicated by the arrows A (i.e., from upstream to downstream). As will be appreciated, however, the flow path 604 may be any other type of flow path, such as a mud pit (i.e., used for drilling fluids and the like) or any other containment or storage vessel, and the sample substance 602 may not necessarily be flowing in the direction A while the sample substance 602 is being monitored. As such, portions of the flow path 604 may be arranged substantially vertical, substantially horizontal, or any directional configuration therebetween, without departing from the scope of the disclosure.

The optical computing device 600 may be configured to determine a characteristic of interest in the sample substance 602 or a component present within the sample substance 602. In some embodiments, the device 600 may include an electromagnetic radiation source 608 configured to emit or otherwise generate electromagnetic radiation 610. The electromagnetic radiation source 608 may be any device capable of emitting or generating electromagnetic radiation, such as, but not limited to, a light bulb, a light emitting diode (LED), a laser, a blackbody, a photonic crystal, an X-Ray source, combinations thereof, or the like. In some embodiments, a lens 612 may be configured to collect or otherwise receive the electromagnetic radiation 610 and direct a beam 614 of electromagnetic radiation 610 toward the sample substance 602. In other embodiments, the lens 612 may be omitted from the device 600 and the electromagnetic radiation 610 may instead be directed toward the sample substance 602 directly from the electromagnetic radiation source 608.

In one or more embodiments, the device 600 may also include a sampling window 616 arranged adjacent to or otherwise in contact with the sample substance 602 for detection purposes. The sampling window 616 may be made from a variety of transparent, rigid or semi-rigid materials that are configured to allow transmission of the electromagnetic radiation 610 therethrough. After passing through the sampling window 616, the electromagnetic radiation 610 impinges upon and optically interacts with the sample substance 602, including any components present within the sample substance 602. As a result, optically interacted radiation 618 is generated by and reflected from the sample substance 602. Those skilled in the art, however, will readily recognize that alternative variations of the device 600 may allow the optically interacted radiation 618 to be generated by being transmitted, scattered, diffracted, absorbed, emitted, or re-radiated by and/or from the sample substance 602, without departing from the scope of the disclosure.

The optically interacted radiation 618 generated by the interaction with the sample substance 602 may be directed to or otherwise be received by an ICE core 620 arranged within the device 600. The ICE core 620 may be a spectral component substantially similar to the ICE core 100 described above with reference to FIG. 1 and fabricated using one of the methods 200, 500 of FIGS. 2 and 5, respectively, as discussed above. Accordingly, in operation the ICE core 620 may be configured to receive the optically interacted radiation 618 and produce modified electromagnetic radiation 622 corresponding to a particular characteristic of the sample substance 602. In particular, the modified electromagnetic radiation 622 is electromagnetic radiation that has optically interacted with the ICE core 620, whereby an approximate mimicking of the regression vector corresponding to the characteristic of the sample substance 602 is obtained.

While FIG. 6 depicts the ICE core 620 as receiving reflected electromagnetic radiation from the sample substance 602, the ICE core 620 may be arranged at any point along the optical train of the device 600, without departing from the scope of the disclosure. For example, in one or more embodiments, the ICE core 620 (as shown in dashed lines) may be arranged within the optical train prior to the sampling window 616 and equally obtain substantially the same results. Moreover, in other embodiments, the ICE core 620 may generate the modified electromagnetic radiation 622 through reflection, instead of transmission therethrough.

The modified electromagnetic radiation 622 generated by the ICE core 620 may subsequently be conveyed to a detector 624 for quantification of the signal. The detector 624 may be any device capable of detecting electromagnetic radiation, and may be generally characterized as an optical transducer. In some embodiments, the detector 624 may be, but is not limited to, a thermal detector such as a thermopile or photoacoustic detector, a semiconductor detector, a piezo-electric detector, a charge coupled device (CCD) detector, a video or array detector, a split detector, a photon detector (such as a photomultiplier tube), photodiodes, combinations thereof, or the like, or other detectors known to those skilled in the art.

In some embodiments, the detector 624 may be configured to produce an output signal 626 in real-time or near real-time in the form of a voltage (or current) that corresponds to the particular characteristic of interest in the sample substance 602. The voltage returned by the detector 624 is essentially the dot product of the optical interaction of the optically interacted radiation 618 with the respective ICE core 620 as a function of the concentration of the characteristic of interest of the sample substance 602. As such, the output signal 626 produced by the detector 624 and the concentration of the characteristic may be related, for example, directly proportional. In other embodiments, however, the relationship may correspond to a polynomial function, an exponential function, a logarithmic function, and/or a combination thereof.

In some embodiments, the device 600 may include a second detector 628, which may be similar to the first detector 624 in that it may be any device capable of detecting electromagnetic radiation. The second detector 628 may be used to detect radiating deviations stemming from the electromagnetic radiation source 608. Undesirable radiating deviations can occur in the intensity of the electromagnetic radiation 610 due to a wide variety of reasons and potentially causing various negative effects on the device 600. These negative effects can be particularly detrimental for measurements taken over a period of time. In some embodiments, radiating deviations can occur as a result of a build-up of film or material on the sampling window 616 which has the effect of reducing the amount and quality of light ultimately reaching the first detector 624. Without proper compensation, such radiating deviations could result in false readings and the output signal 626 would no longer be primarily or accurately related to the characteristic of interest.

To compensate for these types of undesirable effects, the second detector 628 may be configured to generate a compensating signal 630 generally indicative of the radiating deviations of the electromagnetic radiation source 608, and thereby normalize the output signal 626 generated by the first detector 624. As illustrated, the second detector 628 may be configured to receive a portion of the optically interacted radiation 618 via a beamsplitter 632 in order to detect the radiating deviations. In other embodiments, however, the second detector 628 may be arranged to receive electromagnetic radiation from any portion of the optical train in the device 600 in order to detect the radiating deviations, without departing from the scope of the disclosure.

In some applications, the output signal 626 and the compensating signal 630 may be conveyed to or otherwise received by a signal processor 634 communicably coupled to both the detectors 624, 628. The signal processor 634 may be a computer including a processor and a machine-readable storage medium having instructions stored thereon, which, when executed by the processor 634, cause the optical computing device 600 to perform a number of operations, such as determining a characteristic of interest of the sample substance 602. For instance, the concentration of each characteristic detected with the optical computing device 600 can be fed into an algorithm operated by the signal processor 634. The algorithm can be part of an artificial neural network configured to use the concentration of each detected characteristic in order to evaluate the overall characteristic(s) or quality of the sample substance 602.

The signal processor 634 may also be configured to computationally combine the compensating signal 630 with the output signal 626 in order to normalize the output signal 626 in view of any radiating deviations detected by the second detector 628. In real-time or near real-time, the signal processor 634 may be configured to provide a resulting output signal 636 corresponding to a concentration of the characteristic of interest in the sample substance 602.

Figure 7:
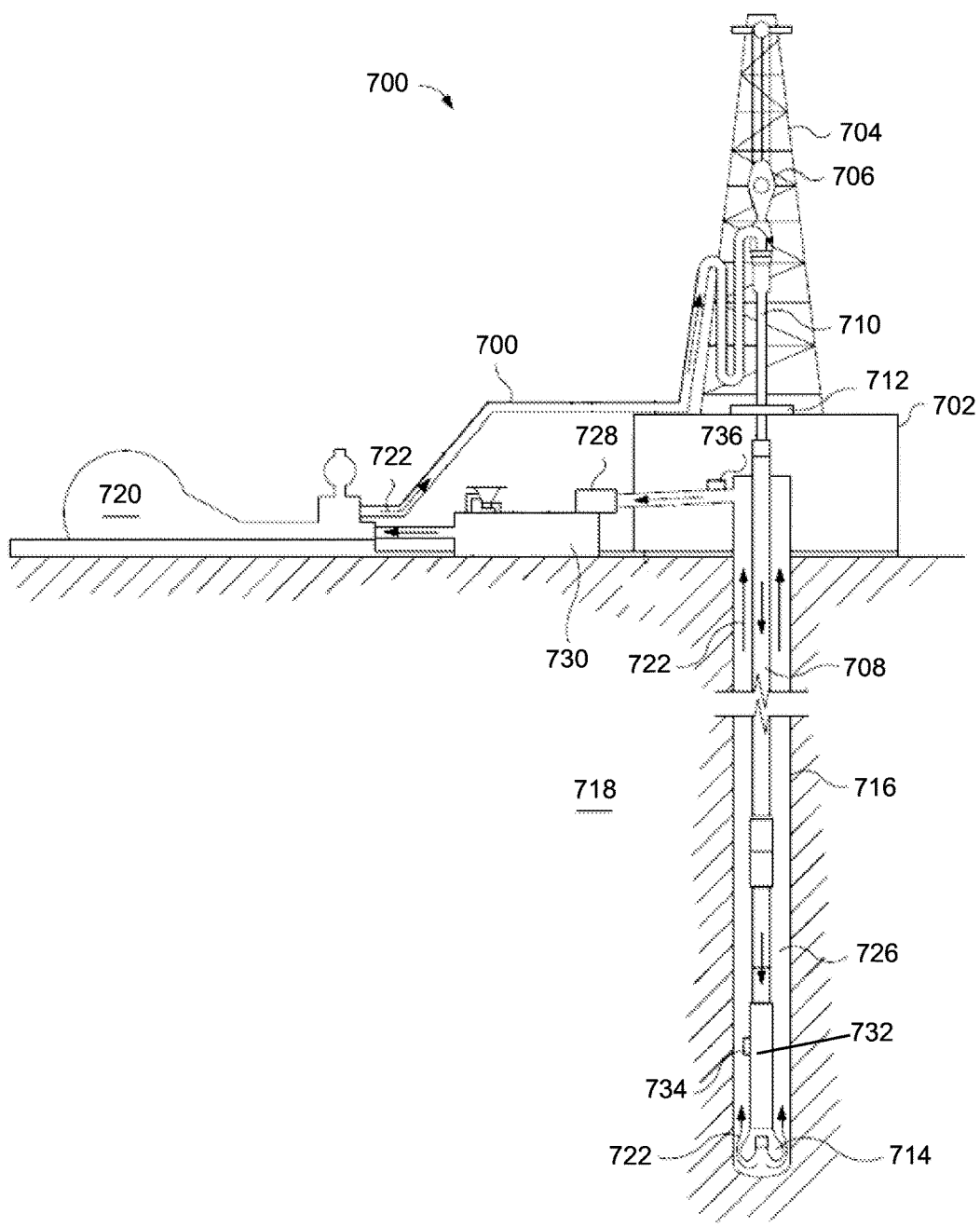
FIG. 7 illustrates an exemplary wellbore drilling assembly that may employ one or more optical computing devices for monitoring a downhole substance, according to one or more embodiments.

Referring now to FIG. 7, with continued reference to FIG. 6, illustrated is an exemplary wellbore drilling assembly 700 that may employ the optical computing device 600 of FIG. 6, including the ICE core 620, in order to monitor a drilling operation, according to one or more embodiments. The drilling assembly 700 may include a drilling platform 702 that supports a derrick 704 having a traveling block 706 for raising and lowering a drill string 708. A kelly 710 supports the drill string 708 as it is lowered through a rotary bit 714. A drill bit 714 is attached to the distal end of the drill string 708 and is driven either by a downhole motor and/or via rotation of the drill string 708 from the well surface. As the bit 714 rotates, it creates a borehole 716 that penetrates various subterranean formations 718.

A pump 720 (e.g., a mud pump) circulates drilling fluid 722 through a feed pipe 724 and to the kelly 710, which conveys the drilling fluid 722 downhole through an interior conduit defined in the drill string 708 and through one or more orifices in the drill bit 714. The drilling fluid 722 is then circulated back to the surface via an annulus 726 defined between the drill string 708 and the walls of the borehole 716. At the surface, the recirculated or spent drilling fluid 722 exits the annulus 726 and may be conveyed to one or more solids control equipment 728 via an interconnecting flow line and subsequently to a retention pit 730. The drilling fluid 722 may then be recirculated back downhole via the pump 720.

A bottom hole assembly (BHA) 732 may be in in the drill string 708 at or near the drill bit 714. The BHA 732 may include any of a number of sensor modules, which may include formation evaluation sensors and directional sensors, such as measuring-while-drilling and/or logging-while-drilling tools. The BHA 732 may further include at least one optical computing device 734, similar to the optical computing device 600 of FIG. 6. The optical computing device 734 may be configured to monitor the drilling fluid 722 within the annulus 726 as it returns to the surface. The optical computing device 734 may include at least one ICE core (not shown) substantially similar to the ICE cores 100, 600 described above and fabricated using one of the methods 200, 500 of FIGS. 2 and 5, respectively, as discussed above. In some embodiments, the drilling assembly 700 may further include another optical computing device 736 may be arranged to monitor the drilling fluid 722 as it is recirculated or otherwise exits out of the borehole 716. The optical computing device 734 may also include at least one ICE core (not shown) substantially similar to the ICE cores 100, 600 described above and fabricated using one of the methods 200, 500 of FIGS. 2 and 5, respectively, as discussed above.

While the optical computing devices 734, 736 are depicted as being used in conjunction with a the drilling assembly 700, it will be appreciated that one or both of the optical computing devices 734, 736 may be used in conjunction with several other downhole tools in obtaining a variety of downhole measurements. For instance, the optical computing devices 734, 736 may be used in conjunction with, but not limited to, a sampling tool of a wireline application, a measurement device associated with production tubing, etc., without departing from the scope of the disclosure.

Embodiments disclosed herein include:

A. A method that includes providing a substrate that has at least a first surface and a second surface opposite the first surface, depositing multiple optical thin films on the first and second surfaces of the substrate via a thin film deposition process, and thereby generating a multilayer film stack device, cleaving the substrate to produce at least two optical thin film stacks, and securing one or more of the at least two optical thin film stacks to a secondary optical element for use as an integrated computational element (ICE).

B. A method that includes providing a substrate, depositing multiple optical thin films on a surface of the substrate via a thin film deposition process and thereby generating an optical thin film stack, removing at least a portion of the substrate from the optical thin film stack, and securing the optical thin film stack to a secondary optical element for use as an integrated computational element (ICE).

C. A system that includes a downhole tool extendable within a wellbore penetrating a subterranean formation, and an optical computing device arranged on the downhole tool and configured to monitor a substance within the wellbore, the optical computing device including at least one integrated computational element (ICE) that has been fabricated according to the following steps: providing a substrate that has at least a first surface and a second surface substantially opposite the first surface, depositing multiple optical thin films on the first and second surfaces of the substrate via a thin film deposition process, and thereby generating a multilayer film stack device, and cleaving the substrate to produce at least two optical thin film stacks, wherein one of the at least two optical thin film stacks is the at least one ICE.

Each of embodiments A, B, and C may have one or more of the following additional elements in any combination: Element 1: wherein the substrate is planar. Element 2: where the substrate is at least one of mica, pyrolitic carbon, graphite, and graphene. Element 3: wherein depositing the multiple optical thin films on the substrate is preceded by preparing the first and second surfaces of the substrate. Element 4: wherein preparing the first and second surfaces of the substrate comprises reducing a thickness of the substrate either chemically or mechanically. Element 5: wherein preparing the first and second surfaces of the substrate comprises chemically treating at least one of the first and second surfaces so that it becomes more receptive to the thin film deposition process. Element 6: wherein the thin film deposition process is an atomic layer deposition (ALD) process, and wherein depositing the multiple optical thin films on the first and second surfaces of the substrate comprises suspending the substrate within an ALD reaction chamber, and sequentially growing the multiple optical thin film layers on both of the first and second surfaces of the substrate. Element 7: wherein a first optical thin film layer of the multiple optical thin film layers is made of a metal oxide. Element 8: further comprising depositing the first optical thin film layer to a thickness that is greater than an adjacent optical thin film layer. Element 9: wherein cleaving the substrate is preceded by subdividing the multilayer film stack device into multiple optical thin film units. Element 10: wherein securing the one or more of the at least two optical thin film stacks to the secondary optical element is preceded by removing the substrate from the one or more of the at least two optical thin film stacks. Element 11: further comprising chemically removing the substrate from the one or more of the at least two optical thin film stacks by at least one of subjecting the substrate to low temperature oxidation, combusting the substrate, and dissolving the substrate in a solvent bath. Element 12: wherein securing the one or more of the at least two optical thin film stacks to the secondary optical element comprises at least one of using an adhesive, sintering edges of the one or more of the at least two optical thin film stacks, and melting a target surface of the secondary optical element. Element 13: wherein securing the one or more of the at least two optical thin film stacks to the secondary optical element comprises chemically reacting the substrate of the one or more of the at least two optical thin film stacks, and melting a target surface of the secondary optical element to bond the one or more of the at least two optical thin film stacks to the secondary optical element.

Element 14: wherein depositing the multiple optical thin films on the substrate is preceded by preparing the surface of the substrate either chemically or mechanically. Element 15: wherein securing the optical thin film stack to the secondary optical element is preceded by subdividing the optical thin film stack into multiple optical thin film stacks. Element 16: wherein removing the at least a portion of the substrate from the optical thin film stack is preceded by securing the optical thin film stack to the secondary optical element. Element 17: further comprising chemically reacting the substrate and thereby melting a target surface of the secondary optical element to bond the optical thin film stack to the secondary optical element. Element 18: wherein removing the portion of the substrate from the optical thin film stack comprises chemically removing the substrate from the optical thin film stack by at least one of subjecting the substrate to low temperature oxidation, combusting the substrate, and dissolving the substrate in a solvent bath. Element 19: wherein the secondary optical element is a component of an optical computing device selected from the group consisting of a sector of a filter wheel, a band pass filter, a lens, a surface of an optical fiber, a sampling window, a sapphire optical element, a non-planar optical element, and a detector. Element 20: wherein securing the optical thin film stack to the secondary optical element comprises at least one of using an adhesive, sintering edges of the optical thin film stack, and melting a target surface of the secondary optical element. Element 21: wherein securing the optical thin film stack to the secondary optical element comprises chemically reacting the substrate of the optical thin film stack and thereby melting a target surface of the secondary optical element to bond the optical thin film stack to the secondary optical element.

Element 22: wherein the at least one ICE is secured to a secondary optical element of the optical computing device, and wherein the secondary optical element is a component selected from the group consisting of a sector of a filter wheel, a band pass filter, a lens, a surface of an optical fiber, a sampling window, a sapphire optical element, a non-planar optical element, and a detector. Element 23: wherein the downhole tool is a tool selected from the group consisting of a bottom hole assembly, a sampling tool of a wireline application, and a measurement device associated with production tubing.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A method, comprising:
providing a substrate that has at least a first surface and a second surface substantially opposite the first surface;
depositing multiple optical thin films on the first surface and the second surface of the substrate via a thin film deposition process, wherein each of the multiple optical thin films is deposited simultaneously on the first surface and on the second surface of the substrate;
cleaving the substrate with a planar cut, the planar cut parallel to the first surface and the second surface, to produce at least two optical thin film stacks and thereby generating at least two multilayer film stack devices comprising a first optical thin film stack formed on the first surface and a second optical thin film stack formed on the second surface, wherein each layer in the first optical thin film stack mirrors a corresponding layer in the second optical thin film stack, and wherein each of the at least two multilayer film stack devices is suitable for use in a same optical computing device; and
securing one or more of the at least two optical thin film stacks to a secondary optical element for use as an integrated computational element (ICE).

2. The method of claim 1, wherein the substrate is planar.

3. The method of claim 2, where the substrate is at least one of mica, pyrolitic carbon, graphite, and graphene.

4. The method of claim 1, wherein depositing the multiple optical thin films on the substrate is preceded by preparing the first surface and the second surface of the substrate.

5. The method of claim 4, wherein preparing the first surface and the second surface of the substrate comprises reducing a thickness of the substrate either chemically or mechanically.

6. The method of claim 4, wherein preparing the first surface and the second surface of the substrate comprises chemically treating at least one of the first surface and the second surface so that it becomes more receptive to the thin film deposition process.

7. The method of claim 1, wherein the thin film deposition process is an atomic layer deposition (ALD) process, and wherein depositing the multiple optical thin films on the first surface and the second surface of the substrate comprises:
suspending the substrate within an ALD reaction chamber; and
sequentially depositing the multiple optical thin films on both of the first surface and the second surface of the substrate.

8. The method of claim 7, wherein a first optical thin film of the multiple optical thin films is made of a metal oxide.

9. The method of claim 8, further comprising depositing a first optical thin film layer to a thickness that is greater than an adjacent optical thin film layer.

10. The method of claim 1, wherein cleaving the substrate is preceded by subdividing the multiple optical thin films into multiple optical thin film units.

11. The method of claim 1, wherein securing the one or more of the at least two optical thin film stacks to the secondary optical element is preceded by removing the substrate from the one or more of the at least two optical thin film stacks.

12. The method of claim 11, further comprising chemically removing the substrate from the one or more of the at least two optical thin film stacks by at least one of subjecting the substrate to low temperature oxidation, combusting the substrate, and dissolving the substrate in a solvent bath.

13. The method of claim 1, wherein securing the one or more of the at least two optical thin film stacks to the secondary optical element comprises at least one of using an adhesive, sintering edges of the one or more of the at least two optical thin film stacks, and melting a target surface of the secondary optical element.

14. The method of claim 1, wherein securing the one or more of the at least two optical thin film stacks to the secondary optical element comprises:
chemically reacting the substrate of the one or more of the at least two optical thin film stacks; and
melting a target surface of the secondary optical element to bond the one or more of the at least two optical thin film stacks to the secondary optical element.

* * * * *